United States Patent
Jiang

(10) Patent No.: US 10,159,462 B2
(45) Date of Patent: Dec. 25, 2018

(54) CATHETER WITH ULTRASOUND SENSOR AND METHOD FOR CREATING A VOLUME GRAPHIC BY MEANS OF THE CATHETER

(71) Applicant: SIEMENS AKTIENGESELLSCHAFT, Munich (DE)

(72) Inventor: Yuan Jiang, Singapore (SG)

(73) Assignee: Siemens Healthcare GmbH, Erlangen (DE)

( * ) Notice: Subject to any disclaimer, the term of this patent is extended or adjusted under 35 U.S.C. 154(b) by 573 days.

(21) Appl. No.: 13/952,728

(22) Filed: Jul. 29, 2013

(65) Prior Publication Data

US 2014/0039294 A1 Feb. 6, 2014

(30) Foreign Application Priority Data

Jul. 31, 2012 (DE) .................. 10 2012 213 456

(51) Int. Cl.
*A61B 5/05* (2006.01)
*A61B 8/12* (2006.01)
(Continued)

(52) U.S. Cl.
CPC ............ *A61B 8/12* (2013.01); *A61B 8/4254* (2013.01); *A61B 8/466* (2013.01); *A61B 8/5261* (2013.01); *A61B 8/5292* (2013.01); *A61B 8/483* (2013.01)

(58) Field of Classification Search
None
See application file for complete search history.

(56) References Cited

U.S. PATENT DOCUMENTS

| 2006/0036167 A1* | 2/2006 | Shina | ................ A61B 6/12 600/433 |
| 2006/0173299 A1* | 8/2006 | Romley | ................ A61B 8/12 600/433 |

(Continued)

FOREIGN PATENT DOCUMENTS

| DE | 102005050344 A1 | 5/2007 |
| DE | 102006011255 A1 | 9/2007 |

(Continued)

OTHER PUBLICATIONS

Peng Wang, Terrence Chen, Olivier Ecabert, Simone Prummer, Martin Ostermeier and Donn Comaniciu, Image-Based Device Tracking for the Co-registration of Angiography and Intravascular Ultrasound Images, Medical Image Computing and Computer-Assisted Intervention—MICCAI 2011, Lecture Notes in Computer Science, 2011, vol. 6891/2011, pp. 161-168, 2011.

(Continued)

*Primary Examiner* — Amelie R Gillman
(74) *Attorney, Agent, or Firm* — Lempia Summerfield Katz LLC

(57) ABSTRACT

A method is provided for creating a volume graphic via a catheter for introduction into a vessel which has an ultrasound unit, which is embodied to transmit ultrasound, to measure an echo of the transmitted ultrasound, and to create image data for a two-dimensional cross-section of the vessel on the basis of the measured echo. The method involves creating image data of a cross-section with the ultrasound unit at a plurality of different positions on a movement track of the catheter, and, in addition to the image data, creating position data for the current position of the ultrasound unit with a localization device. The method further involves creating the volume graphic from the image data of all (Continued)

cross-sections in which the cross-sections are arranged relative to one another in accordance with the position data.

6 Claims, 6 Drawing Sheets

(51) Int. Cl.
*A61B 8/00* (2006.01)
*A61B 8/08* (2006.01)

(56) References Cited

U.S. PATENT DOCUMENTS

| | | | |
|---|---|---|---|
| 2007/0038061 A1 | 2/2007 | Burgess | |
| 2008/0146942 A1* | 6/2008 | Dala-Krishna | A61B 6/12 600/466 |
| 2009/0005668 A1* | 1/2009 | West | A61B 6/466 600/407 |
| 2009/0036775 A1* | 2/2009 | Ikuma | A61B 5/06 600/443 |
| 2010/0239150 A1* | 9/2010 | Ishikawa | A61B 5/0095 382/131 |

FOREIGN PATENT DOCUMENTS

| | | |
|---|---|---|
| DE | 102006050886 A1 | 5/2008 |
| WO | WO 2012011035 A1 | 1/2012 |

OTHER PUBLICATIONS

Shengxian Tu, Niels R Holm, Gerhard Koning, Zheng Huang, Johan H C Reiber, Fusion of 3D QCA and IVUS/OCT, Int J Cardiovasc Imaging Feb. 2011, 27(2) pp. 197-207 , 2011.

Shlomo A Ben-Haim, Daniel Osadchy, Israel Schuster, Lior Gepstein, Gal Hayam, and Mark E Josephson, Nonfluoroscopic, in vivo navigation and mapping technology, Nature Med , vol. 2, No. 12, pp. 1393-1395,, 1996.

Lior Gepstein and Steven J Evans,, L , Electroanatomical mapping of the heart Basic concepts and implications for the treatment of cardiac arrhythmias, Pacing and Clinical Electrophysiology, vol. 21, No. 6, pp. 1268-1278, 1998.

Christopher Piorkowski and Gerhard Hindricks, Nonfluoroscopic Sensor-Guided Navigation of Intracardiac Electrophysiology Catheters Within Prerecorded Cine Loops, Circulation Arrhythmia and Electrophysiology 2011, 4, pp. e36-e38, 2011.

Terrence Chen, Terrence Chen, Image-Based tracking technologies, Tutorial of Image guided interventions, MICCAI 2011 Tutorial on Image-Guided Interventions Morning Session, http //campar in turn de/twiki/pub/IGI/WebHome/Chen_ImageBasedTracking_MICCAI_2011 pdf, 2011.

* cited by examiner

FIG 5
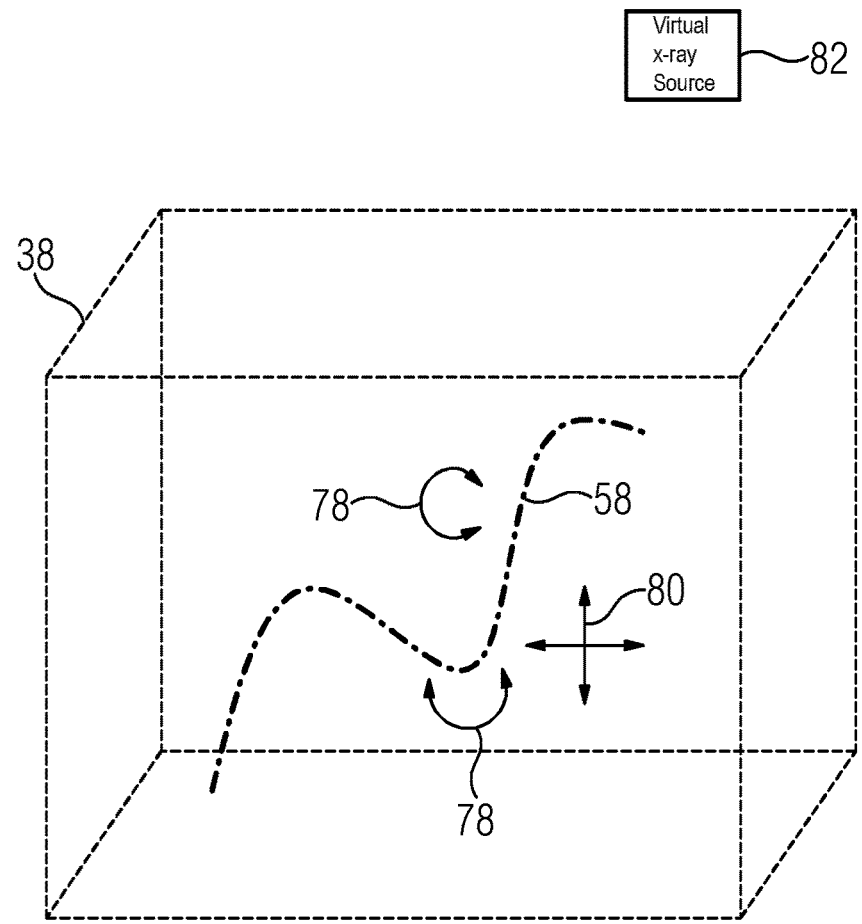
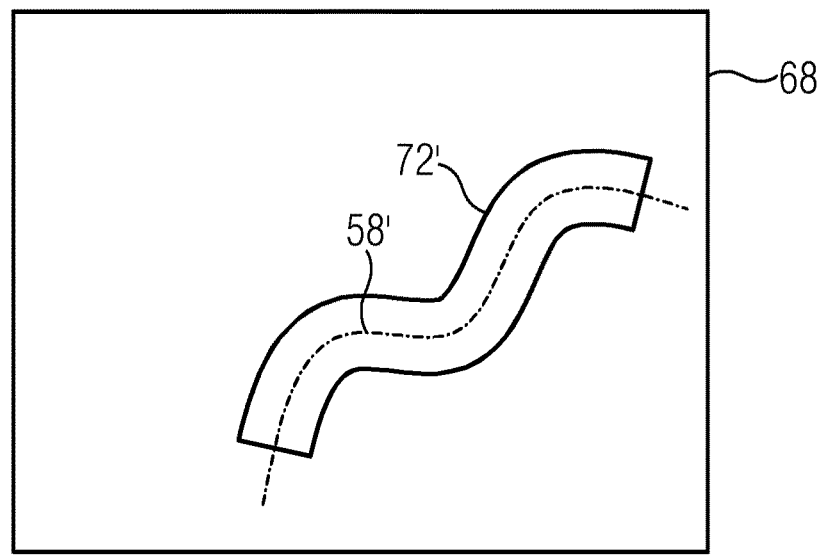

CATHETER WITH ULTRASOUND SENSOR AND METHOD FOR CREATING A VOLUME GRAPHIC BY MEANS OF THE CATHETER

CROSS REFERENCE TO RELATED APPLICATIONS

The present application claims priority to German Patent Office application No. 102012213456.5 DE filed Jul. 31, 2012, the entire content of which is hereby incorporated herein by reference.

FIELD OF INVENTION

The invention relates to a catheter with an ultrasound sensor for an intravascular ultrasound (IVUS) examination. The invention also includes a method for recording an image of a vessel such as a blood vessel for example with a catheter, which is to be introduced into the vessel for said purpose. Finally the invention also includes an imaging system.

BACKGROUND OF INVENTION

IVUS examination is a medical modality which makes it possible, from the inside of a blood vessel, to examine the inner side of the blood vessel and its wall. For this purpose an ultrasound unit, which is embodied to transmit ultrasound and to measure an echo of the transmitted ultrasound, can be disposed on the tip of the catheter to be introduced into the blood vessel. Image data for a two-dimensional cross-section of the vessel is then created on the basis of the measured echo. In the cross-section the blood surrounding the catheter, the inner side of the vessel wall and if necessary a further part of the wall itself can be recognized. The IVUS technology is preferably employed in the catheter-based interventional examination of coronary arteries. It offers a doctor the option of obtaining images for the artery wall from inside the vessel, which particularly enables constrictions of the arteries (stenoses) to be detected. The disadvantage of IVUS technology however is that the doctor is only shown a cross-section of the blood vessel very restricted in its location. This makes it difficult for the observer to obtain an overview.

A second modality for examining blood vessels is angiography. In this modality the blood vessels are x-rayed by means of an x-ray device and thus a projection of the vessel (angiogram) is obtained in the form of 2D image data. 2D image data is to be understood here and below as data which describes the individual pixels or picture elements of one or more color intensity values in each case for a gray value or for a color value.

To enable the blood vessels to be better recognized in the projection a contrast medium can be injected into the blood vessels. Projections of the blood vessels, on the basis of which the structure of the vessel can be recognized, can in fact be obtained by means of angiography. It is disadvantageous however that details of individual stenoses are not reproduced for instance with the same high local resolution as is possible by means of IVUS technology. The resolution capabilities of angiographic systems are not sufficient for this purpose.

SUMMARY OF INVENTION

The object of the present invention is to make it possible to more closely examine the details of vessels of a body, especially of blood vessels.

The object is achieved by the features of the independent claims. Advantageous developments of the invention are defined by the features of the dependent claims.

The inventive method is based on the use of a catheter with an ultrasound unit, as was described at the start. In order to record an image of a tubular object in three dimensions using this method, the catheter is moved along a movement track, or track for short, within the tubular object, e.g. within a vessel of a human or animal body or within pores in a porous material or within a tube system. For clearer presentation of the invention it is presumed below that the catheter is being moved through a blood vessel. However the invention only relates to the processing of the signals of the catheter. In the method image data of a cross-section of the vessel is obtained with the ultrasound unit at a number of different positions along the track. For this purpose the movement of the catheter can be interrupted if necessary.

In the inventive method, each time image data is obtained by means of the ultrasound unit for a cross-section of the vessel, in addition to the image data, position data for the current position of the ultrasound unit is also created, i.e. coordinates for example. This is carried out by a localization device. Localization devices of this type are already known from the prior art. A localization device suitable for this purpose can for example be realized by a magnetic sensor being integrated into the catheter, by means of which a magnetic field is measured, which is generated by one or more sources in an environment of the catheter and of the vessel to be examined. For example a number of differently oriented coils can be disposed in the magnetic sensor, by means of which the magnetic field strength of magnetic alternating fields of different sources is measured in different orientation directions. On the basis of the measurements the distances to the individual sources can be deduced and thereby the position of the magnetic sensor. With a known distance between magnetic sensor and ultrasound sensor, position data for the position of the ultrasound sensor can thus be determined.

As a further step of the inventive method there is now provision for creating a volume graphic from the image data of all cross-sections, in which the cross-sections are disposed in accordance with the position data relative to one another. In visual terms the slice-type cross-sections are stacked onto one another in the volume graphic, so that a complete image of the vessel is produced again.

The volume graphic can for example be provided in the form of 3D image data. 3D image data is to be understood here as a dataset comprising data for individual volume elements (voxel-volume elements) of the imaged volume. For each volume element in this case an intensity value for a gray tone can be specified or a number of intensity values for a color tone of the volume graphic can be specified.

The inventive method has the advantage that the correctly-positioned assembly of the individual cross-sections for a volume graphic enables a complete spatial anatomical structure of a blood vessel to be reconstructed. The volume graphic represents a three-dimensional reconstruction of the blood vessel and of the environment of said vessel, i.e. a volume model. The imaging precision corresponds in such cases to that which is able to be achieved by IVUS technology.

In a development of the inventive method, in addition to the position data, orientation data is created in each case for the cross-sections for a current spatial orientation of the ultrasound sensor. For example a normal vector to the cross-sectional plane in which the cross-section was determined can be determined. In the volume graphic the cross-sections will then not only be disposed in accordance with the assigned position, but will also be tilted in relation to one another in accordance with the orientation data. This enables a wounded blood vessel with a bent course to be imaged very precisely.

In accordance with another embodiment of the method there is provision for interpolating 3D image data for which no image data of a cross-section exists, in the volume graphic between individual cross-sections. This enables a complete volume model of a vessel to also be computed from the individual slice-shaped cross-sections even if the positions of the cross-sections are spaced comparatively far apart.

In accordance with another development of the method there is provision for a center line of the vessel, or generally of the object through which the catheter is moved, to be defined from the position data of the cross-sections and/or from further, additionally recorded position data. Such a center line offers an important orientation aid for automated image analysis by an image analysis program, for example the measuring of the lumen of the vessel.

The volume graphic obtained from the ultrasound examination by means of the image data can also be used in an advantageous manner to add missing details into image data which was created by means of another modality, for example by means of angiography. To this end an embodiment of the method makes provision, through a prespecified projection specification, for example an algorithm for a forward projection, for creating a simulated or artificial projection of at least one object of the volume graphic. This artificial projection is again described by 2D image data, similar to that of an angiogram itself. This 2D image data of the projection of the object is referred to here as 2D projection data.

The entire anatomical structure represented by the volume graphic can be used as a basis for the object which is mapped by means of the artificial projection. It can however also be a blood vessel isolated by means of a segmentation but also just the aforementioned center line. The projection can in this case occur a number of times and can occur iteratively such that a position of the at least one object is changed until the projection of the object covers the further projection of the same object obtained by means of the other modality. In this way a blood vessel imaged in the volume graphic can be made to coincide with an image of the same blood vessel in an angiogram.

If, instead a vessel or the like, only the center line itself is projected, this is naturally not absolutely necessarily present in the further projection, i.e. in an angiogram for example. Therefore there can also be provision to make the projection of the center line coincide with another prespecified object from the further projection for example.

"Coincide" is to be understood in connection with the invention as there being a difference between the artificial projection of the object from the volume graphic on the one hand and the further projection from the other modality on the other hand of less than a prespecified threshold value, i.e. as there being a predetermined degree of coverage. As a measure for the coverage in this case the overall deviation for summing the amounts of the differences from the square of the differences can be used as a basis by means of a subtraction of the intensity values of individual pixels. An iterative algorithm for controlling the change of position can for example be a minimum mean square error algorithm.

This development of the method produces imaging parameters for the 3D image data of the volume graphic through which it is described how objects in the volume graphic are to be changed in their location so that a projection of these objects is produced which coincides with the projection from the other modality. A 3D-2D registration of the 3D image data of the volume graphic on the one hand and of the 2D image data of the other modality on the other hand is realized by this method.

In connection with the imaging of a coronary artery a further difficulty arises in that the shape of the vessel changes with the heartbeat. To this end an embodiment of the method makes provision for recording times at which in each case image data of a cross-section and the associated position data is obtained to be defined by a signal of an EKG device (electrocardiogram device). The heart muscle activity is measured by means of the EKG device. The signal thus specifies at which points in time the heart is in which phase of a cyclic contraction. Preferably the image data is obtained for all cross-sections in the same phase of the cyclic heart muscle movement. When the cross-sections are merged into a volume graphic the shape of the vessel for this phase of the heart muscle movement is then advantageously obtained.

As already stated at the start, the invention also includes a catheter having an ultrasound sensor for an IVUS examination. The catheter additionally features a positioning unit which is embodied to exchange a position signal with an external localization unit which is dependent on a position of the positioning unit in relation to the external localization unit. For example the location unit can involve the magnetic sensor already described which measures the magnetic field which is generated by the single or the multiple magnetic sources of an external localization unit. Depending on the spatial position at which the magnetic sensor measures the field, this field has a different characteristic amplitude and/or a different time curve and/or a different orientation. From the measured characteristic of the field (amplitude, time curve, orientation) the position and if necessary the orientation of the positioning unit with regard to the external localization unit is then determined. The magnetic field represents the signal in this case. Electromagnetic positioning is also possible. The positioning unit of the catheter can also be designed as a transmitter for the signal.

The invention finally includes an imaging system with an embodiment of the inventive catheter and a localization unit different from the catheter which is designed to exchange a position signal with the positioning unit of the catheter. The signal is preferably exchanged by non-contact means, i.e. by means of electromagnetic or magnetic signals for example. An optical solution is also possible, if for example optical markers are made on the catheter at a location which is not introduced into the vessel. The imaging system further includes an evaluation unit which can comprise a computer for example. The evaluation unit is designed to receive image data from the ultrasound sensor of the catheter and in addition to the image data, also to receive from the positioning unit and/or from the external localization unit position data for the current position of the positioning unit. The evaluation unit is further designed to create a volume graphic from the image data of all cross-sections in which the cross-sections are disposed relative to one another in accordance with the position data.

The invention also includes developments of the inventive imaging system having features which have already been described in conjunction with the developments of the inventive method. For this reason the features of these developments of the inventive imaging system are not described once again here.

BRIEF DESCRIPTION OF THE DRAWINGS

The invention will be explained once again in greater detail below with reference to concrete exemplary embodiments, in which FIG. 5 shows a sketch for a 3D-2D registration of the volume graphic from FIG. 3 with the angiogram from FIG. 4.

DETAILED DESCRIPTION OF INVENTION

The examples represent preferred embodiment variants of the invention.

In the examples explained below, the components of the embodiment variants and the steps of the method described each represent features of the invention to be considered individually, independently of one another, which each also develop the invention independently of one another and are thus also to be regarded individually or in a combination other than that shown as a component of the invention. Furthermore the described embodiment variants are also able to be supplemented by further features of the invention which have already described.

Figure 1:
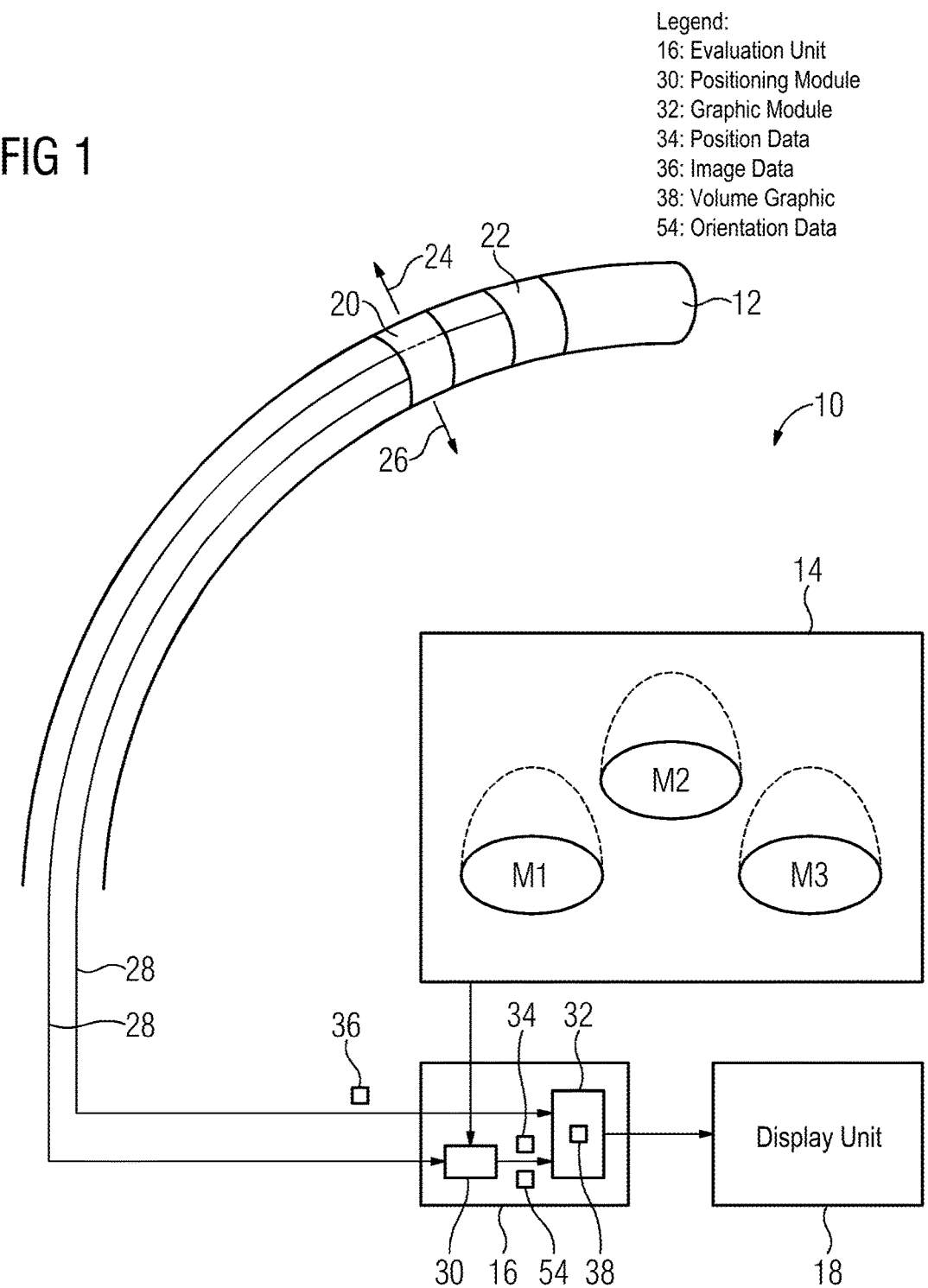
FIG. 1 shows a schematic diagram of an embodiment of the inventive imaging system.

FIG. 1 shows an imaging system 10 having a catheter 12, a localization unit 14, an evaluation unit 16 and a display unit 18. The imaging system 10 can for example be embodied to create a three-dimensional model, i.e. a volume model, from a blood vessel in a body of a human or an animal.

Only a tip of the catheter 12 is shown in FIG. 1, which in accordance with specifications is to be introduced into an object to be examined, for example a blood vessel. The tip of the catheter 12 can be designed in a known manner. An ultrasound unit 20 and in addition also a positioning unit 22 are located on the catheter 12 at its tip.

The ultrasound unit 20 can be embodied in a known manner for an IVUS examination. To this end it can feature a sound source for ultrasound and an acousto-electric converter for measuring the echo of the ultrasound. The ultrasound can be emitted radially from the surface of the catheter 12, for example in radial directions 24, 26.

The positioning unit 22 can for example involve a magnetic sensor which comprises three cylindrical coils disposed orthogonally to one another, by means of which an amplitude and a direction of a magnetic field can be measured. Such a magnetic field can for example be created by means of three sources M1, M2 and M3 for a magnetic field which can be a component of the localization unit 14.

The ultrasound unit 20 and the positioning unit 22 can for example be connected via cables 28 to the evaluation unit 16. The evaluation unit 16 can for example be a computer system. The evaluation unit 16 can feature a positioning module 30 and a graphic module 32.

The positioning module 30 is designed to receive signals from the positioning unit 22 via one of the cables 28 and if necessary also to receive signals from the localization unit 14 and to determine from the received signals a relative location of the positioning unit 22 in relation to the sources M1, M2 and M3. On the basis of the determined relative location and on the basis of a relative geometrical offset of the positioning unit 22 to the ultrasound unit 20, the position of the ultrasound unit 20, for example in a coordinate system of the localization unit 14, is computed by the location module 30 and is transferred to the graphic module 32. Through this position data 34 of the ultrasound unit 20 is created by the location module 30.

The ultrasound unit 20 transfers image data 36 to the graphic module 32 via a further cable 28. The image data 36 is created from the echo of the emitted ultrasound received and measured by the ultrasound unit 20.

Instead of the localization unit 14 and the localization module 30, a localization system integrated into an angiography system can also be used for a catheter. Furthermore, instead of magnetic sources M1, M2, M3, another positioning technology can be used, which for example can be based on the emission of electromagnetic signals. Accordingly the positioning unit 22 is then an electromagnetic receiver. The positioning unit 22 can also be a transmitter for signals which are then received by the localization units 14 and can be evaluated in relation to the position of the positioning unit 22.

Through the graphic module 32 the volume module for the vessel being examined is created from the position data 34 and the image data 36 and stored as a volume graphic 38. The volume graphic 38 can be displayed to a doctor for example via the display unit 18. The display unit 18 can for example be a screen.

An explanation is given below with reference to FIG. 2 and FIG. 3 of how image data 36 is obtained and volume graphic 38 created by the graphic module 32 on the basis of the position data 34 and the image data 36.

Figure 2:
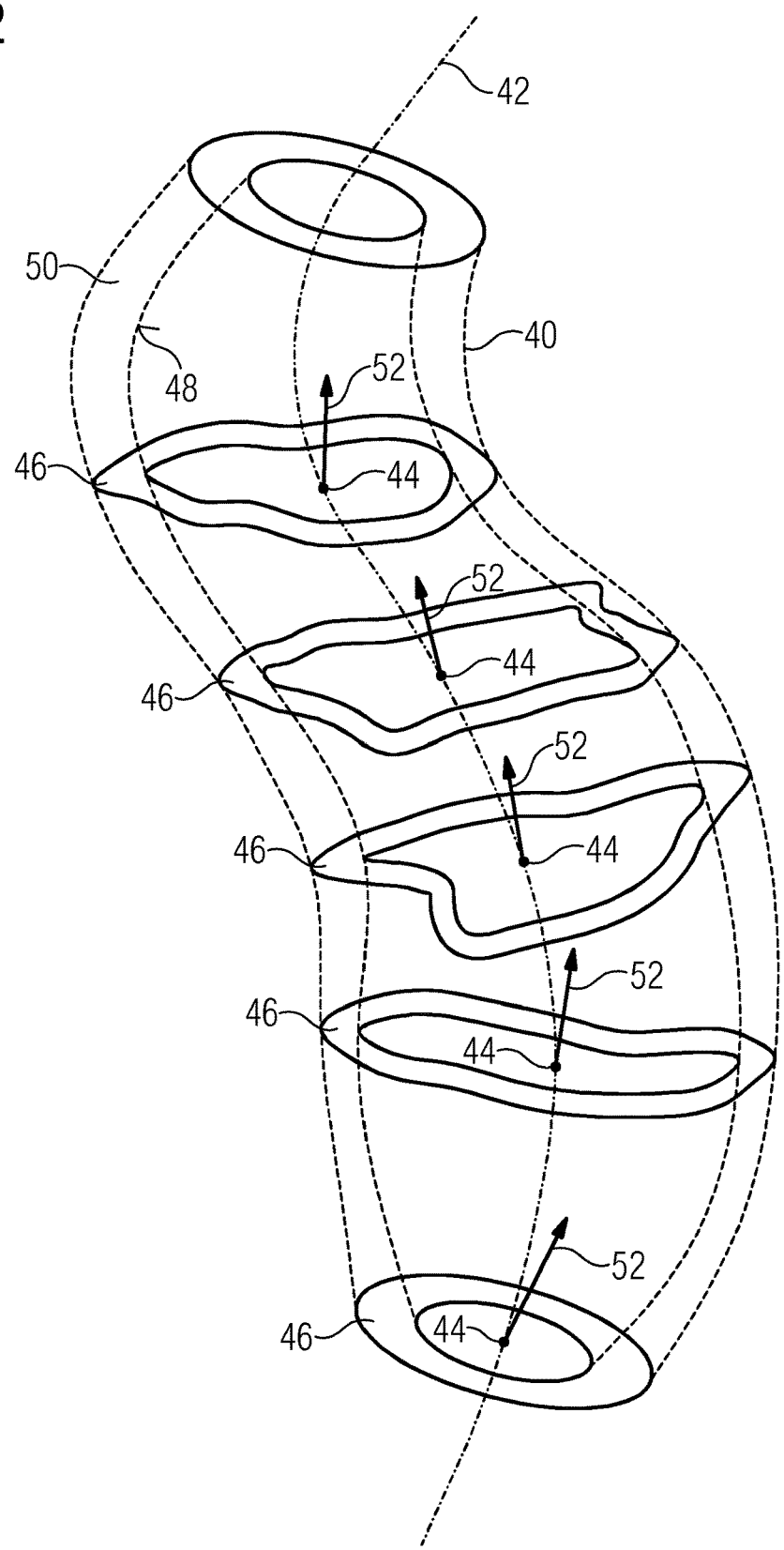
FIG. 2 shows a blood vessel in which image data for cross-sections of the blood vessel is determined by means of the imaging system.

The blood vessel 40 examined in the underlying example by means of an imaging system 10 is shown in FIG. 2. FIG. 2 shows the situation after the image data 36 and the position data 34 have been obtained by means of the catheter 12. The catheter 12 was moved along a course or a path or a track 42 through the blood vessel 40. At a number of different positions 44 along the track 42 image data 36 is created by means of the ultrasound unit 20 for a cross-section 46 of the vessel 40 by the ultrasound unit 20. In FIG. 2 the cross-sections 46 are illustrated in each case as the sectional set of the points which was produced between the plane in which the cross-section 46 was obtained and the blood vessel 40. In the image data of each cross-section 46 the blood present in the vessel 40 around the catheter 12, an internal surface 48 of the vessel 40, a vessel wall 50 of the vessel 40 itself and if necessary also a part of the body tissue surrounding the vessel wall 50 are visible.

Signals are also generated in each case by the positioning unit 22 for the individual positions 44, from which the positioning module 30 creates position data 34 for the positions 44. In addition there can be provision for a spatial orientation 52 of the positioning unit 22 to be created by the positioning module 30 from the signals of the positioning unit 22 and thus the plane of the cross-section 46. This can likewise be transferred as orientation data 54 from the localization module 30 to the graphic module 32. The spatial orientation 52 is represented in each case by a normal vector of the cross-sectional plane in FIG. 2.

Figure 3:
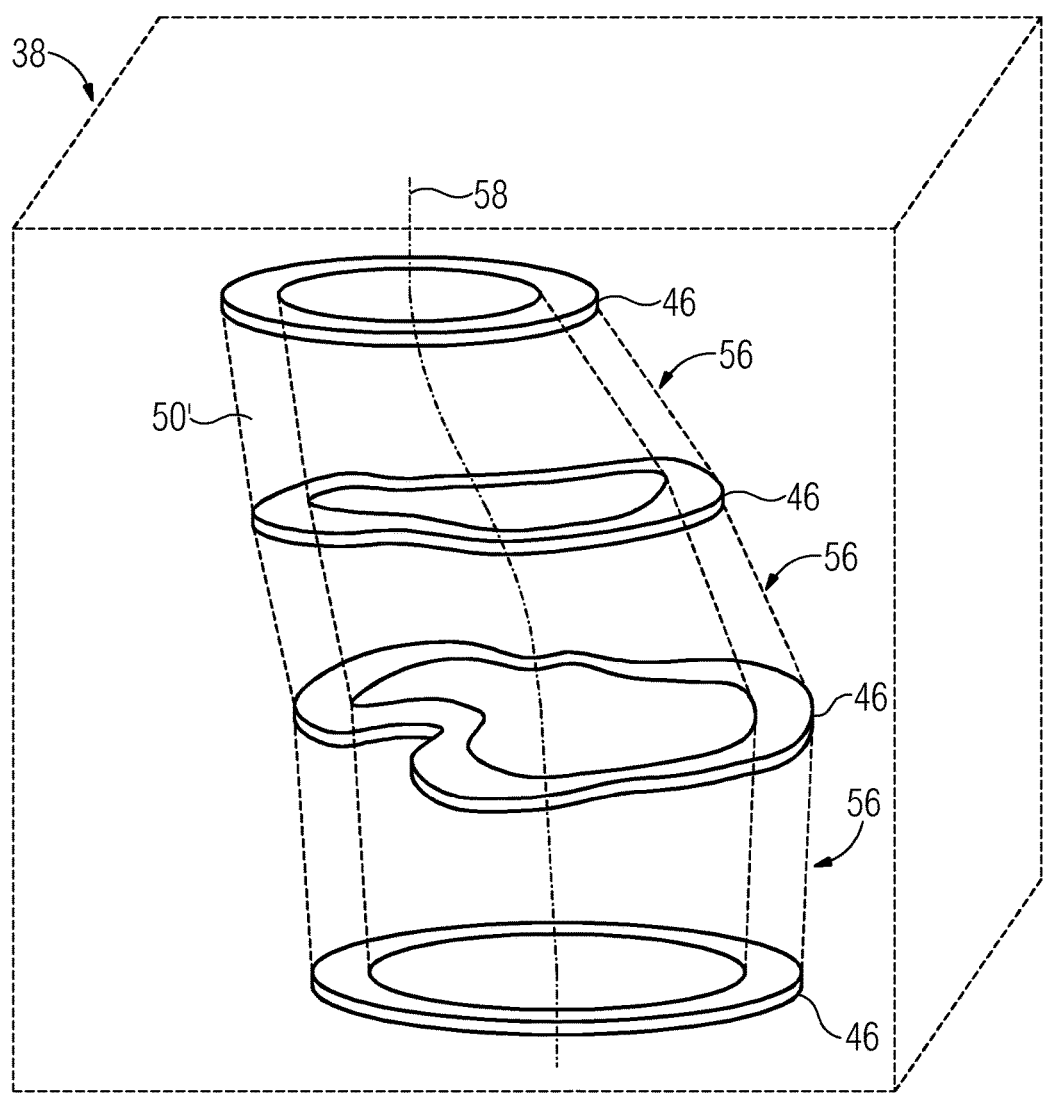
FIG. 3 shows a schematic diagram of a volume graphic which was created by means of the cross-sections.

A volume graphic 38 is shown in FIG. 3, as exists digitally for example as a 3D image dataset and may have been created by the graphic module 32 from the image data 36, the position data 34 and if necessary the orientation data 54.

In the volume graphic 38 the cross-sections 46 can be arranged relative to one another as slices from volume elements in the manner as is produced by the position data 34. In other words the position of the cross-sections 46 in the volume graphic 38 was defined in accordance with the relative positions 44 of the imaging points along the track 42. Further volume elements made up of interpolated 3D image data can be inserted between the cross-sections 46, so that a comprehensive image 50' of the wall 50 of the vessel 40 is provided from the image data 34 and the inserted volume elements 46 in the volume graphic 38. Data for a course of a center line 58 of the vessel 40 can also be a component of the volume graphic 38. The center line 58 can for example be formed from the position data 34 for the positions 44 or also from further position data for further positions along the track 42.

The volume graphic 38 can be presented to a doctor as a display option on the display device 18. However the detailed resolution of another presentation, e.g. of an angiogram, can also be improved by means of the volume graphic 38. How this can be achieved is explained below with reference to FIG. 4 and FIG. 5.

Figure 4:
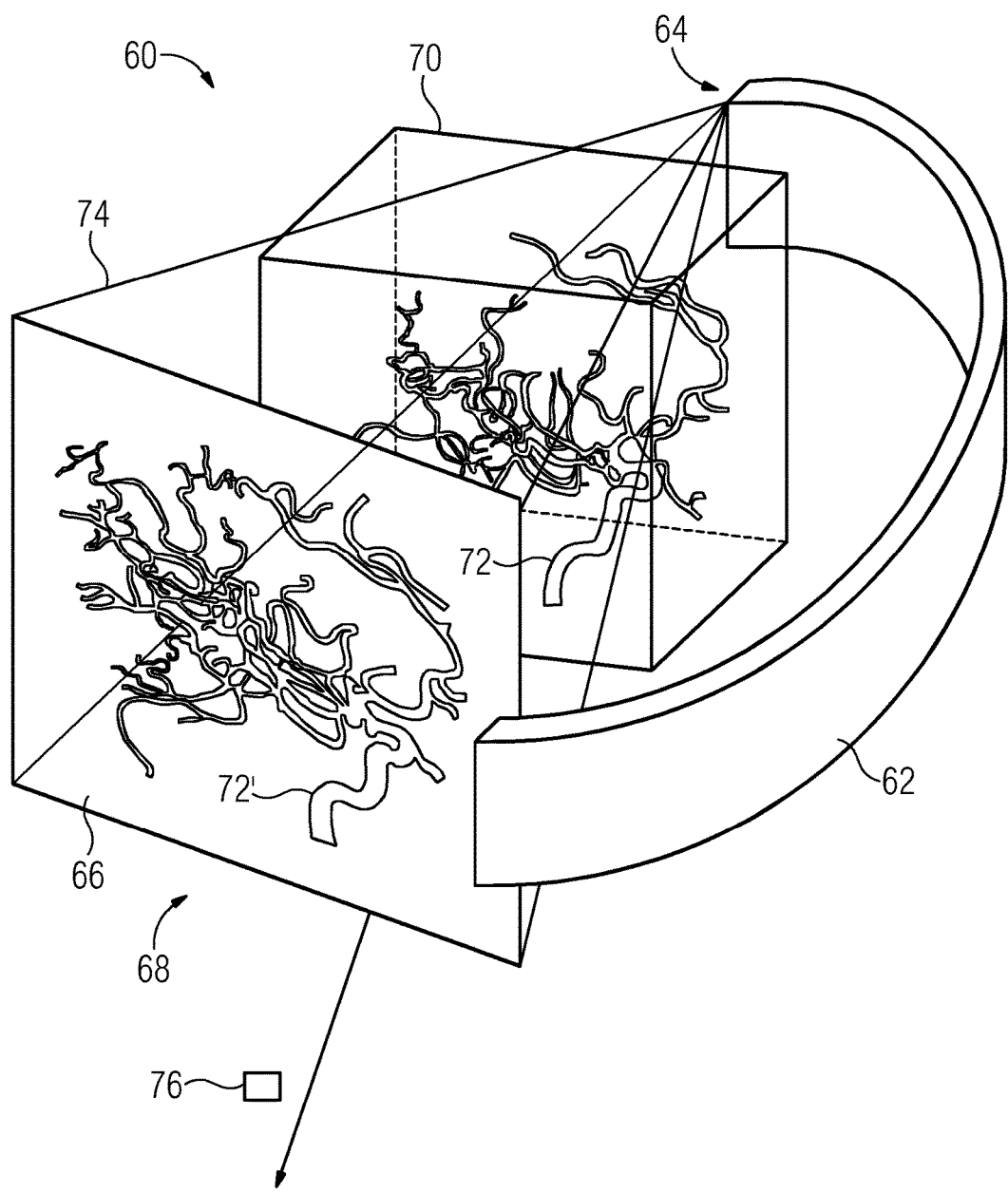
FIG. 4 shows a sketch to illustrate an angiography by means of which an angiogram is obtained.

FIG. 4 shows an angiography system 60 which comprises a C-arm 62, on one end of which an x-ray radiation source or x-ray source 64 for short (not shown in any greater detail) and on the other end of which an x-ray image detector 66, for example a flat-panel detector are disposed. An angiogram 68 is created by means of the angiography system 60. To this end the x-ray source 64 x-rays a body 70, for example the body of a human being, while an x-ray-dense contrast medium is flowing in the blood vessels 72 in the body 70. The x-rays of the x-ray source 64 form an x-ray cone beam 74, through which a two-dimensional projection 72' of the blood vessels 72 is created on the x-ray image detector 66. 2D image data 76 of the projection of the blood vessels 72 created therefrom by the x-ray image detector 66 forms the angiogram 68. The 2D image data 76 can for example be transmitted to the evaluation unit 16.

FIG. 5 shows how the angiogram 68 is registered with the volume model 38 of a 3D-2D registration. To this end for example there can be provision for changing the center line 58 in an iterative method through rotations 78 and translations 80 in its position in relation to a virtual x-ray source 82 and after each change of position, for creating a two-dimensional projection 58' by simulating an x-ray image with the virtual x-ray source 82. A scaling of the center line 58 is also possible in order to adapt the size of its projection 58'. A course of the projection 58' of the center line 58 can then be compared with the projections 72' of the blood vessels 72 in the angiogram 68. By the position of the center line 58 being changed iteratively in the volume graphic 38 and a new projection 58' being created, a position for the center line 58 can thus be determined in which the projection 58' of the center line 58 and the projection 72' of the blood vessels coincide in their courses. Subsequently the entire volume model 38 or the model 50' of the vessel 40 can then be inserted via a further projection into the angiogram 68 correctly dimensioned and positioned. Then those details which are visible by means of the ultrasound in the volume model 38 are also able to be recognized in the angiogram 68. An automated isolation of the 3D image data of the model 50' in the volume graphic 38 is possible for example by means of a segmentation.

For a doctor the imaging system 10 is able to be used in combination with the angiograph 60 in the following way for example in a workflow. Such a workflow can for example be carried out by a doctor in an American hospital who wishes to undertake a cardiological examination on a patient and for this purpose wishes to examine a coronary artery by means of the catheter 12 and the angiograph 60. In this case the vessel 40 is then the coronary artery.

Figure 6:
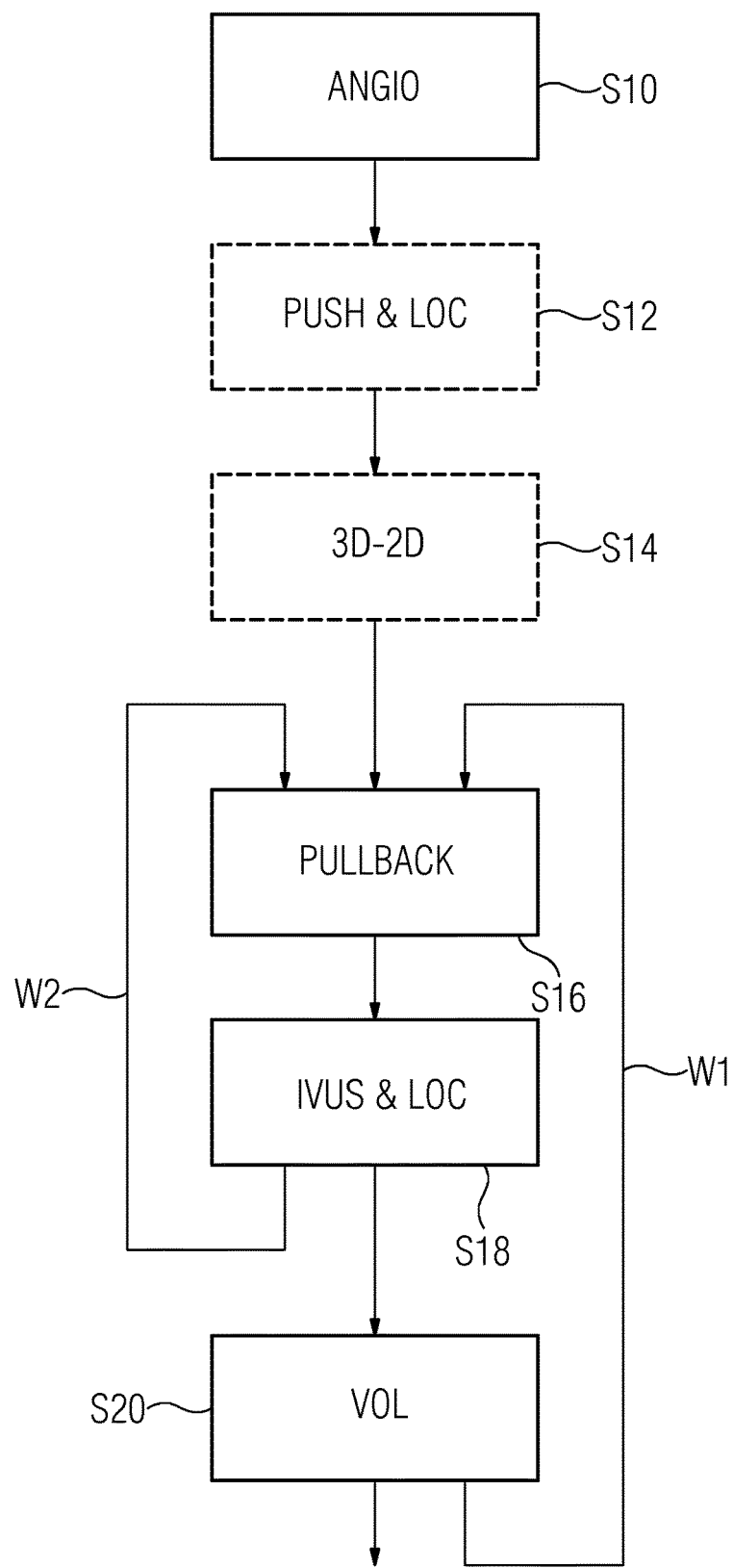
FIG. 6 shows a flow diagram for an execution sequence of an embodiment of the inventive method.

The method comprises the following steps (see FIG. 6):

s10) Creation of the angiogram 68 by the angiography system 60 (ANGIO);

s12) Pushing the catheter 12 into the blood vessel 40 (PUSH) and, in doing so, creating location data (LOC) along the track 42 in the blood vessel 40 and creating the center line (58);

s14) Carrying out the 3D-2D registration of the center line 58 with the angiogram 68 (as described in connection with FIG. 5).

s16) Pulling the catheter 12 back in the blood vessel 40 along the track 42 (PULLBACK) and, in doing so, interrupting the movement at the positions 44 if necessary;

s18) Obtaining image data 36 for a cross-section 46 at the positions 44 in each case by means of the ultrasound sensor 20 and detecting the position data for the positions 44 by means of the positioning unit 22;

s20) Displaying the volume graphic 38 by means of the display unit 18.

Steps s12 and s14 are optional. If the steps s12 and s14 are executed it is possible to display the volume graphic 38 as an overlay in the angiogram 68.

The volume graphic 38 can be constructed step-by step in that, by a repetition W1 after the image data 36 has been obtained for an individual cross-section 46, initially the volume model 38 is expanded in the step s20 by this cross-section and subsequently the pullback is continued in the step s16. There can also be provision for initially creating the complete volume graphic 38 from all cross-sections 46. To this end a direct repetition W2 of the steps s16 and s18 then takes place after each cross-section 46 is obtained and only after all image data 36 and the associated position data 34 has been obtained is the volume graphic 38 then executed in an individual processing pass in the step s20.

The examples show how, by the combination of IVUS technology, angiography and a navigation system for a catheter, the anatomy of the coronary arteries can be reconstructed in the 3D space, by the current coordinates of the IVUS catheter being determined. Through this the system presented makes possible a precise, real-time-capable and automated registration between IVUS image data and angiography image data, for example during an interventional re-canalization of coronary arteries.

The invention claimed is:

1. A method for creating a volume graphic of a vessel by an image system, wherein the image system comprises a catheter introduced into the vessel, wherein the catheter comprises an ultrasound unit, wherein the ultrasound unit is configured to transmit ultrasound, to measure an echo of the transmitted ultrasound, and to create image data for a two-dimensional cross-section of the vessel on the basis of the measured echo, the method comprising:

obtaining a plurality of image data of a plurality of different cross-sections of the vessel with the ultrasound unit at a plurality of different positions along a movement track of the catheter within the vessel, measuring a strength of a magnetic field by a magnetic sensor being integrated into the catheter, wherein the magnetic field is generated by a magnetic source, determining a distance of the magnetic sensor relative to the magnetic source from the measurement by a computer, determining, from the distance, position data by the computer for the plurality of different positions of the ultrasound unit when obtaining the plurality of image data, creating the volume graphic from the plurality of image data of the cross-sections, wherein the cross-sections in the volume graphic are arranged relative to one another in accordance with the position data, defining a center line of the vessel from the position data, creating a simulated 2D projection of the center line of the vessel by simulating an x-ray image with a virtual x-ray source, obtaining a projection of the vessel by an angiography system, comparing the simulated 2D projection of the center line of the vessel with the projection of the vessel obtained by the angiography system, changing positions of the center line of the vessel through rotations and translations in relation to the virtual x-ray source and creating a new simulated 2D projection of the center line of the vessel based on the comparison; and repeating the comparing, the changing, and the creating until a course of the new simulated 2D projection of the center line of the vessel coincides with a course of the projection of the vessel obtained by the angiography system.

2. The method as claimed in claim 1, further comprising:
creating orientation data for a plurality of different spatial orientations of the ultrasound unit when obtaining the plurality of image data, wherein the cross-sections in the volume graphic are tilted relative to one another in accordance with the orientation data.

3. The method as claimed in claim 1, further comprising interpolating image data of a cross-section of the vessel in the volume graphic between the cross-sections from the obtained image data.

4. The method as claimed in claim 1, wherein recording times for obtaining the image data of the cross-sections and for obtaining the associated position data are defined by a signal of an electrocardiogram (EKG) device measuring heart muscle activity.

5. An imaging system, comprising:
a catheter that is configured to move along a movement track within a vessel, the catheter comprising an ultrasound sensor and a magnetic sensor,
a magnetic source configured to generate a magnetic field,
a computer, and
an angiography system configured to obtain an angiogram of the vessel,
wherein the ultrasound sensor is configured to obtain a plurality of image data of a plurality of different cross-sections of the vessel at a plurality of different positions on the movement track,
wherein the magnetic sensor is configured to measure a strength of the magnetic field for the plurality of different positions of the ultrasound sensor when obtaining the plurality of image data,
wherein the computer is configured to:
receive the plurality of image data from the ultrasound sensor,
receive the measured signal from the magnetic sensor,
determine a distance of the magnetic sensor relative to the magnetic source from the measurement,
determine, from the distance, position data for the plurality of different positions of the ultrasound sensor when obtaining the plurality of image data,
create a volume graphic from the image data of the cross-sections, wherein the cross-sections in the volume graphic are disposed relative to one another in accordance with the position data,
define a center line of the vessel from the position data,
create a simulated 2D projection of the center line of the vessel by simulating an x-ray image with a virtual x-ray source,
obtain a projection of the vessel by the angiography system,
compare the simulated 2D projection of the center line of the vessel with the projection of the vessel obtained by the angiography system,
change positions of the center line of the vessel through rotations and translations in relation to the virtual x-ray source and create a new simulated 2D projection of the center line of the vessel based on the comparison, and
repeat the comparison, the change, and the creation until a course of the new simulated 2D projection of the center line of the vessel coincides with a course of the projection of the vessel obtained by the angiography system.

6. The imaging system as claimed in claim 5, further comprising additional magnetic sources configured to generate magnetic fields that are alternated to the magnetic field generated by the magnetic source.

* * * * *